United States Patent
Cuffe et al.

(10) Patent No.: US 8,434,936 B2
(45) Date of Patent: May 7, 2013

(54) METHOD FOR PERFORMING ULTRASONIC TESTING

(75) Inventors: John Michael Cuffe, Reedsville, PA (US); James Barshinger, Niskayuna, NY (US); Ying Fan, Niskayuna, NY (US)

(73) Assignee: GE Inspection Technologies, LP, Lewistown, PA (US)

( * ) Notice: Subject to any disclaimer, the term of this patent is extended or adjusted under 35 U.S.C. 154(b) by 428 days.

(21) Appl. No.: 12/580,345

(22) Filed: Oct. 16, 2009

(65) Prior Publication Data

US 2011/0090935 A1    Apr. 21, 2011

(51) Int. Cl.
*G01K 11/22* (2006.01)

(52) U.S. Cl.
USPC .................. 374/119; 374/100; 374/117

(58) Field of Classification Search ........... 374/117, 374/119
See application file for complete search history.

(56) References Cited

U.S. PATENT DOCUMENTS

| | | | | |
|---|---|---|---|---|
| 3,350,942 A | * | 11/1967 | Peltola | 374/119 |
| 3,633,424 A | * | 1/1972 | Lynnworth et al. | 374/119 |
| 4,483,630 A | * | 11/1984 | Varela | 374/119 |
| 5,596,508 A | * | 1/1997 | Cuffe | 702/171 |
| 5,659,148 A | * | 8/1997 | Isgen | 89/14.05 |
| 5,857,777 A | * | 1/1999 | Schuh | 374/172 |
| 7,726,875 B2 | * | 6/2010 | Yuhas | 374/119 |
| 2004/0258127 A1 | * | 12/2004 | Ramamurthy et al. | 374/117 |
| 2008/0107150 A1 | * | 5/2008 | Brummel et al. | 374/119 |

OTHER PUBLICATIONS

Author: Krishnan Balasubramaniam, Vimal V. Shah, R. Daniel Costley, Gary Boudreaux and Jagdish P. Singh Title: "High temperature ultrasonic sensor for the simultaneous measurement of viscosity and temperature of melts" Date: Dec. 1999 Publisher: American Institute of Physics, Review of Scientific Instruments vol. 70, No. 12 pp. 4618-4623.*

* cited by examiner

*Primary Examiner* — Lisa Caputo
*Assistant Examiner* — Roger Hernandez-Prewitt
(74) *Attorney, Agent, or Firm* — Global Patent Operation; Mark A. Conklin

(57) ABSTRACT

A method for performing ultrasonic testing comprising, in one embodiment, the steps of firing an ultrasonic transducer to generate an ultrasonic pulse that passes through a delay line, measuring a delay echo time of flight, and determining the temperature of the delay line using the delay echo time of flight, thereby eliminating the need for additional temperature measuring devices. Other embodiments further comprise the step of using the temperature of the delay line to determine the temperature of a test object, and using the temperature of the test object to determine a thickness of the test object that is compensated for thermal expansion and temperature dependent ultrasonic velocity.

16 Claims, 3 Drawing Sheets

METHOD FOR PERFORMING ULTRASONIC TESTING

BACKGROUND OF THE INVENTION

This invention relates generally to nondestructive testing, and more particularly to a method for determining the temperature of a test object by ultrasonically measuring the temperature of an ultrasonic delay line in close thermal contact with the test object. Furthermore, this invention relates to the temperature compensation of ultrasonic test measurements using the aforementioned ultrasonic temperature measurement of the test object.

Nondestructive testing devices can be used to inspect test objects to identify and analyze flaws and defects in the objects both during and after an inspection. Nondestructive testing allows an operator to place a probe at or near the surface of the test object in order to perform testing of both the object surface and underlying structure. Nondestructive testing can be particularly useful in some industries, e.g., aerospace, power generation, and oil and gas recovery and refining, where object testing must take place without removing the object from surrounding structures, and where hidden defects can be located in areas that would otherwise not be identifiable through visual inspection.

One example of nondestructive testing is ultrasonic testing. When conducting ultrasonic testing, an ultrasonic pulse can be emitted from a probe and passed through a test object at the characteristic sound velocity of that particular material. The sound velocity of a given material depends mainly on the modulus of elasticity, temperature and density of the material. Application of an ultrasonic pulse to a test object causes an interaction between the ultrasonic pulse and the test object structure, with sound waves being reflected back to the probe. The corresponding evaluation of the signals received by the probe, namely the amplitude and time of flight of those signals, can allow conclusions to be drawn as to the internal quality and properties of the test object (e.g., thickness) without destroying it.

Generally, an ultrasonic testing system includes a probe for sending and receiving signals to and from a test object, a probe cable connecting the probe to an ultrasonic test unit, and a screen or monitor for viewing test results. The ultrasonic test unit can include power supply components, signal generation, amplification and processing electronics, and device controls used to operate the nondestructive testing device. Some ultrasonic test units can be connected to computers that control system operations, as well as test results processing and display. Electric pulses can be generated by a transmitter and can be fed to the probe where they can be transformed into ultrasonic pulses by ultrasonic transducers. Ultrasonic transducers often incorporate piezoelectric materials which can be electrically connected to a pulsing-receiving unit in the form of an ultrasonic test unit. Portions of the surfaces of the piezoelectric materials can be metal coated, forming electrodes that can be connected to the ultrasonic test unit. During operation, an electrical waveform pulse is applied to the electrodes of the piezoelectric material causing a mechanical change in dimension and generating an acoustic wave that can be transmitted through a material such as metal or plastic to which the ultrasonic transducer is coupled. Conversely, when an acoustic wave reflected from the material under inspection contacts the surface of the piezoelectric material, it generates a voltage differential across the electrodes that is detected as a receive signal by the ultrasonic test unit or other signal processing electronics.

The amplitude, timing and transmit sequence of the electrical waveform pulses applied by the pulsing unit can be determined by various control means incorporated into the ultrasonic test unit. The pulse is generally in the frequency range of about 0.5 MHz to about 25 MHz, so it is referred to as an ultrasonic wave from which the equipment derives its name. As the ultrasonic pulses pass through the object, various pulse reflections called echoes occur as the pulse interacts with internal structures within the test object and with the opposite side (backwall) of the test object. The echo signals can be displayed on the screen with echo amplitudes appearing as vertical traces and time of flight or distance as horizontal traces. By tracking the time difference between the transmission of the electrical pulse and the receipt of the electrical signal and measuring the amplitude of the received wave, various characteristics of the material can be determined. Thus, for example, ultrasonic testing can be used to determine material thickness or the presence and size of imperfections within a given test object.

The temperature of a test object impacts both the speed at which an ultrasonic pulse travels through that object and the relative size of that object due to thermal expansion. This limits the ability of the ultrasonic testing system in certain applications, such as determining pipe corrosion rates, as the required degree of accuracy in the thickness measurements is extremely high. Compensating for thermal changes in the test object is currently a manual process requiring calibration of the system based on the temperature of the test object as measured by a thermocouple or pyrometer.

In some applications requiring continuous online monitoring, e.g., as is sometimes required in various plant or refining environments, several to several thousand probes may be positioned throughout a given facility to provide periodic or continuous monitoring of pipe conditions, including the determination of pipe corrosion rates and the identification of specific locations in need of routine maintenance to avoid pipe failures. In conjunction with the ultrasonic probes, a network of thermometers or pyrometers is required in current applications to provide temperature readings of the inspection targets. This added network of thermometers or pyrometers increases both the complexity of the ultrasonic testing system and the costs associated with installing and maintaining such a system.

It would be advantageous to perform ultrasonic measurements of a test object without requiring separate and costly devices for measuring the temperature of the test object. It would also be advantageous to perform ultrasonic measurements of a test object by automatically compensating for the effects of thermal expansion and thermally induced ultrasonic velocity changes on that test object.

BRIEF DESCRIPTION OF THE INVENTION

Methods of performing ultrasonic testing using an ultrasonic testing system with the capability of ultrasonically measuring the temperature of an ultrasonic delay line and/or test object are disclosed. In one embodiment, the method comprises the steps of firing an ultrasonic transducer to generate an ultrasonic pulse that passes through a delay line, measuring a delay echo time of flight, and determining the temperature of the delay line using the delay echo time of flight. In another embodiment, the method comprises the steps of measuring a first temperature of a delay line, firing an ultrasonic transducer to generate a first ultrasonic pulse that passes through the delay line, measuring a first (calibration) delay echo time of flight, firing the ultrasonic transducer to generate a second ultrasonic pulse that passes through the delay line, measuring a second delay echo time of flight, and determining the temperature of the delay line using the first and second delay echo times of flight and the first temperature of the delay line.

In other embodiments, the method of performing ultrasonic testing further comprises the step of using the temperature of the delay line to determine the temperature of a test object. In still further embodiments, the method of performing ultrasonic testing further comprises the step of using the temperature of a test object to determine a thickness of the test object that is compensated for thermal expansion and temperature dependent ultrasonic velocity.

DETAILED DESCRIPTION OF THE INVENTION

Figure 1:
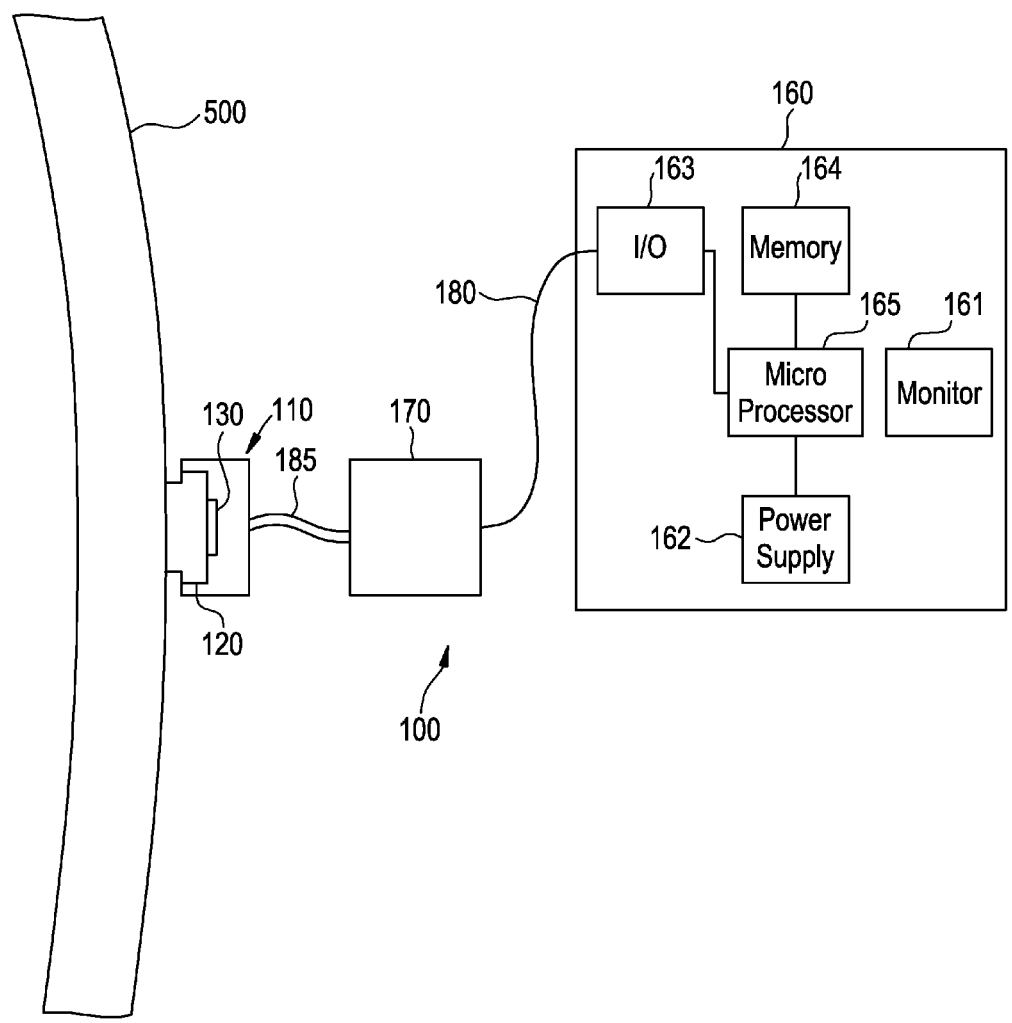
FIG. 1 is a block diagram of an exemplary ultrasonic testing system.

FIG. 1 is a block diagram of an ultrasonic testing system 100 in combination with a test object 500. In one embodiment, ultrasonic testing system 100 can comprise an ultrasonic transducer 110 that can be attached to a delay line 120. Transducer 110 can include an ultrasonic element 130 for transmitting and receiving ultrasonic sound pulses. In some embodiments, the delay 120 can be made integral to the transducer 110. In other embodiments, the delay line 120 can be separately attached to the transducer 110. Transducer 110 and delay 120 can be mechanically attached to the test object 500 using various means (e.g., U-bolts or clamps) to ensure a secure thermocoupling between the delay 120 and the test object 500. Over time, the temperature of the delay line 120 will be the same as that of the test object 500. The delay line 120 can be made from a variety of materials including but not limited to stainless steel, titanium, ceramic, or various alloys, such as INCONEL® available from Specialty Metals Corp. of Huntington, W. Va. In some embodiments, transducer 110 can be replaced with an ultrasonic transducer array (not shown, which, in turn, can be comprised of one or more ultrasonic transducers 110. The amplitude and firing sequence of the individual transducers comprising the array can be controlled in order to adjust the angle and penetration strength of the ultrasonic sound beam that is sent into a test object 500.

Transducer cable 185 can connect the transducer 110 to the ultrasonic testing unit 170. In some embodiments, transducer cable 185 can be constructed of wire able to withstand high and low temperature extremes. Ultrasonic testing unit 170 can comprise a power supply and electrical signal generation and processing electronics.

Ultrasonic pulser and receiver electronics (not shown) can transmit and receive the ultrasonic signals. The received signals are typically processed through some type of analog to digital conversion, after which they are displayed as A-scans with amplitude on the y-axis and time of flight on the x-axis. One or more microprocessors 165 can provide control over the entire process.

Ultrasonic testing unit 170 can be electrically connected to a computer 160 through a cable 180. The computer 160 can include a power supply 162, microprocessor 165 for running system software and controlling system operations, memory 164, an input/output controller 163 for managing data being sent to and from, among other components, the ultrasonic testing unit 170, a keyboard (not shown), a joystick or mouse (not shown), a printer (not shown), and various other peripherals (not shown). Computer 160 can also comprise a monitor 161 for viewing system operations and inspection results.

Figure 2:
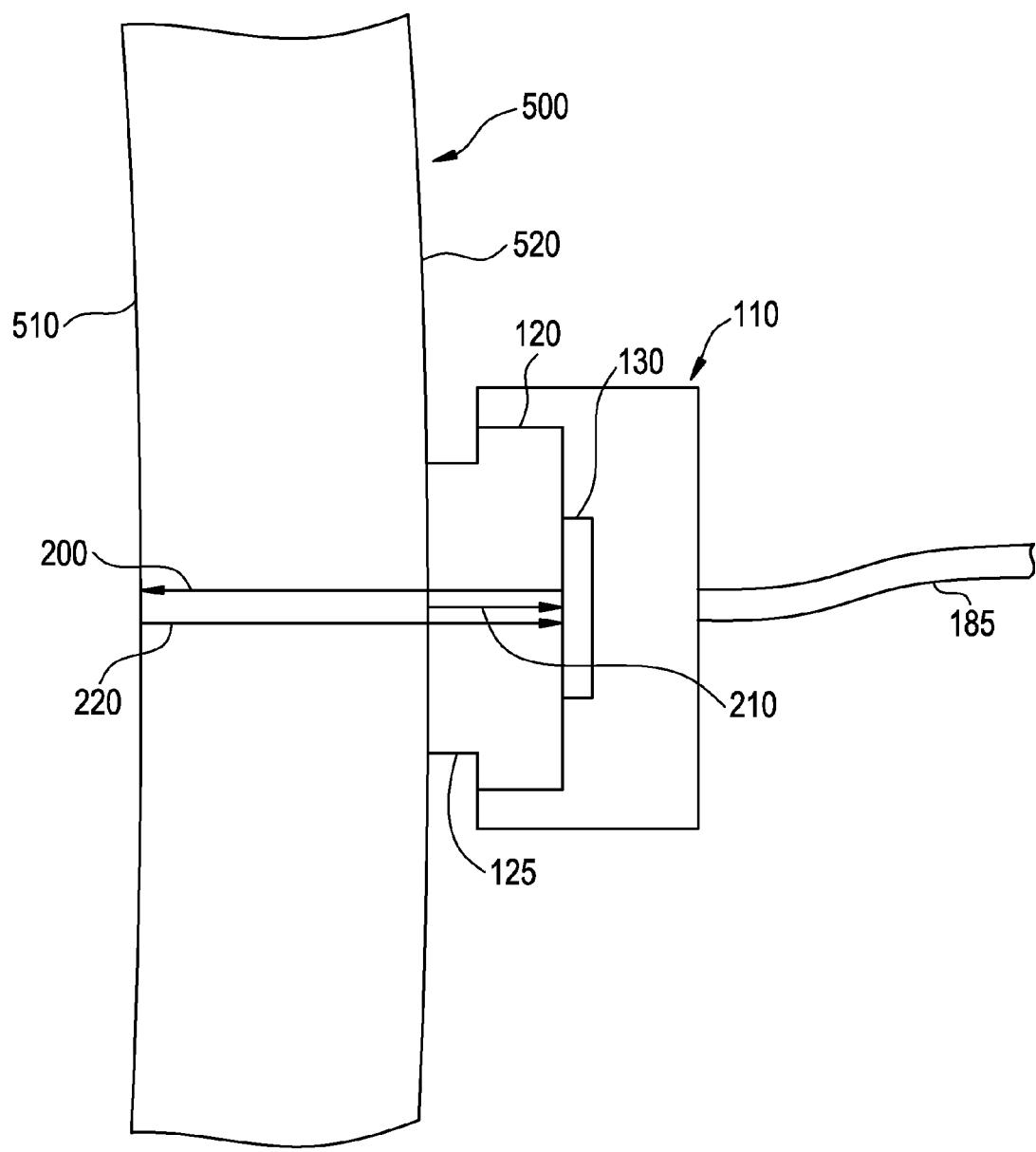
FIG. 2 is a cross sectional diagram of an exemplary ultrasonic probe with delay line installed on a test object.

FIG. 2 is a cross sectional diagram of an ultrasonic testing system 100 positioned on a test object 500 showing an exemplary ultrasonic pulse 200 emanating from the ultrasonic element 130 of transducer 110, through the delay line 120, and through the test object 500. At the delay interface 125 formed at the junction of the outside wall 520 of the test object 500 and the delay line 120, a portion of the ultrasonic pulse 200 is reflected back towards and subsequently sensed by the ultrasonic element 130. This is the delay echo 210. The time it takes for the ultrasonic pulse 200 to hit the delay interface 125 and for the delay echo 210 to travel back to the ultrasonic element 130 is the delay line 120 time of flight. Similarly, a backwall echo 220 is generated when the ultrasonic pulse 200 encounters the backwall 510 of the test object 500. The backwall echo 220 is reflected back towards and is subsequently sensed by the ultrasonic element 130. Subtracting the delay line 120 time of flight from the time it takes for the ultrasonic pulse 200 to hit the backwall 510 and for the backwall echo 220 to travel back to the ultrasonic element 130 is the test object 500 time of flight.

Using ultrasonic techniques, the thickness of a test object 500 can be expressed by Equation 1:

$$L = \frac{1}{2} Ct \qquad (1)$$

wherein,
L=the thickness of the test object 500 at temperature T,
C=the ultrasonic velocity within the test object 500 at temperature T, and
t=the test object 500 time of flight at temperature T.

This formula can be used to determine the thickness of a test object 500 at any temperature given that the ultrasonic velocity, C, is known for a given temperature and the ultrasonic time of flight can be measured. Because of thermal expansion, however, the resulting measured thickness will change as the temperature changes. This can be problematic as a thickness change due to temperature could be mistakenly identified as a change in thickness due to corrosion. This, coupled with the fact that velocity information for a given material over a large temperature range is seldom available, necessitates compensating the thickness readings to a specific temperature, preferably a temperature at which the ultrasonic velocity is well known. This new calculation can be defined as Equation 2:

$$L_{Comp} = \frac{1}{2} C_{Comp} t_{Comp} \qquad (2)$$

wherein,
$L_{Comp}$=the thickness of the test object 500 at temperature $T_{Comp}$,
$C_{Comp}$=the ultrasonic velocity within the test object 500 at temperature $T_{Comp}$, and
$t_{Comp}$=the test object 500 time of flight at temperature $T_{Comp}$.

Equation 2 is useful if the velocity, $C_{Comp}$, and time of flight, $t_{Comp}$, are known at the compensation temperature.

Although the velocity will typically be known, for high temperature applications, the time of flight is a measured value that is known at the operating temperature of the test object being measured. Thus it is necessary to build a relationship between the time of flight at the compensation temperature, $t_{Comp}$, and the time of flight at the measurement temperature, t.

To solve this problem, the relationship between the ultrasonic time of flight at a reference temperature, for convenience, 0° C., $t_0$, and the time of flight at the measurement temperature, t, can be expressed as shown in Equation 3:

$$t_0 = th(T) \quad (3)$$

wherein, $t_0$=the test object 500 time of flight at 0° C., t=the test object 500 time of flight at temperature T, and h(T)=a transfer function relating time of flight at temperature T to the time of flight at 0° C.

Rearranging Equation 3, Equation 4 can be derived:

$$\frac{t}{t_0} = \frac{1}{h(T)} \quad (4)$$

Substituting $t_{Comp}$ for t and $h(T_{Comp})$ for h(T), Equation 5 can be derived:

$$\frac{t_{Comp}}{t_0} = \frac{1}{h(T_{Comp})} \quad (5)$$

By combining Equation 3 and Equation 5, the relationship between $t_{Comp}$ and t can be expressed according to Equation 6:

$$t_{Comp} = t \frac{h(T)}{h(T_{Comp})} \quad (6)$$

Substituting Equation 6 into Equation 2 yields Equation 7, relating $L_{Comp}$, the thickness of the test object 500 at the temperature $T_{Comp}$, to the test object 500 time of flight at temperature T:

$$L_{Comp} = \frac{1}{2} C_{Comp} t \frac{h(T)}{h(T_{Comp})} \quad (7)$$

Adapting Equation 2, the uncompensated thickness of test object 500, $L_u$, can be expressed using the measured time of flight, t, along with the known ultrasonic velocity at the chosen compensation temperature, $C_{Comp}$, yielding Equation 8:

$$L_u = \frac{1}{2} C_{Comp} t \quad (8)$$

Equation 8 is useful in that $L_u$ is the actual, uncompensated, measured thickness of the test object as determined by the ultrasonic testing system 100.

Combining Equations 7 and 8 yields Equation 9:

$$L_{Comp} = L_u \frac{h(T)}{h(T_{Comp})} \quad (9)$$

Equation 9, in turn, provides a compensated thickness value of the test object 500 at a chosen temperature value, allowing direct comparisons of thickness measurements for test object 500 at a user-defined temperature value, $T_{Comp}$, and eliminating the error introduced into test object thickness measurements and analysis by thermal expansion and temperature dependent velocity of the test object 500 at different temperatures.

In order to utilize the relationship between $L_u$ and $L_{Comp}$ established by Equation 9, it is necessary to determine h(T) experimentally for a given material using regression analysis or some other calibration method. For example, using regression analysis, a set of data points containing time of flight versus temperature measurements can be collected experimentally and expressed as $[(t_1,T_1), (t_2,T_2), (t_3,T_3), \ldots (t_n,T_n)]$. In one embodiment, these values can be stored in a table within the ultrasonic testing system 100 for subsequent lookup of temperature, $T_n$, based on a measured time of flight, $t_n$.

Figure 3:
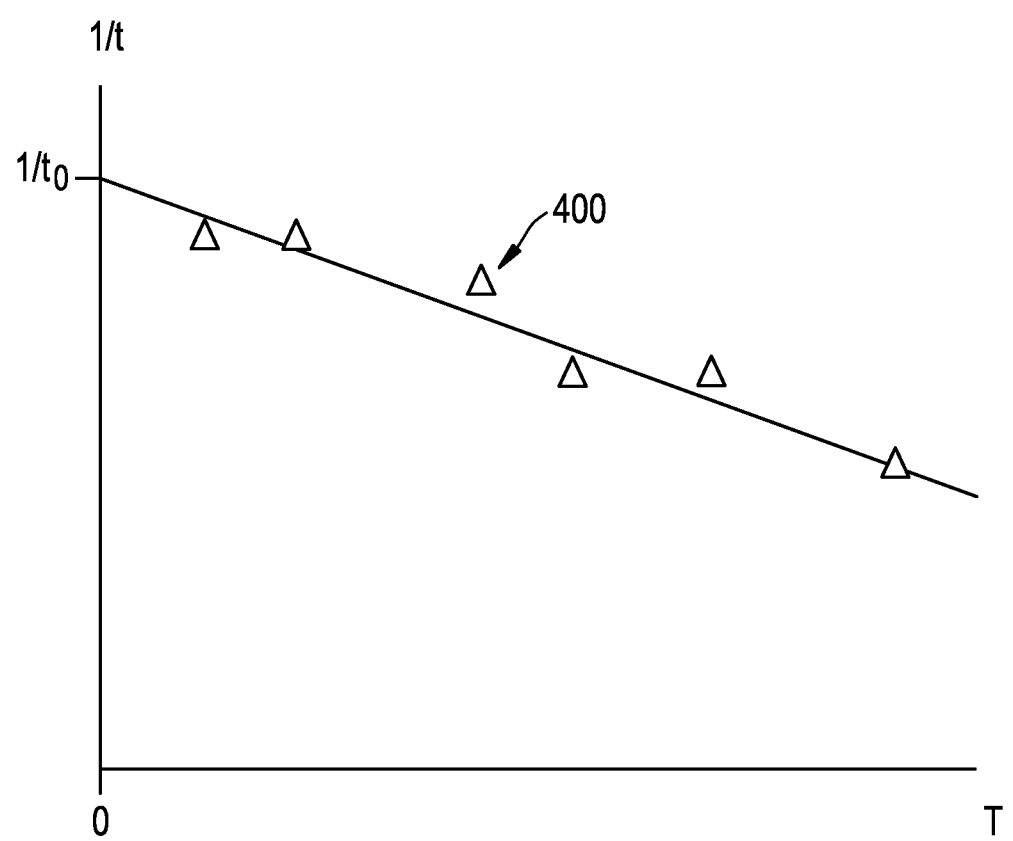
FIG. 3 is an exemplary graph plotting the inverse time of flight of an ultrasonic pulse versus the temperature of the material through which the pulse travels.

Additionally, with reference to FIG. 3, the data points 400, shown as triangles, can be plotted using the inverse of the time of flight versus temperature. In another embodiment, using linear regression analysis, a standard equation of the form of Equation 10 can be fit to the data:

$$y = mx + b \quad (10)$$

wherein, y=1/t, x=T, and b=1/$t_0$.

Substituting these values for y, x and b, Equation 10 yields Equation 11:

$$\frac{t_0}{t} = \left[1 + \frac{m}{b}T\right] \quad (11)$$

wherein m/b can be defined as a compensation coefficient, η. The value of η is a material property and a constant that can be determined for different materials experimentally.

Combining Equations 4 and 11, and using η=m/b, the equation for h(T) can be expressed as Equation 12:

$$h(T) = [1 + \eta T] \quad (12)$$

As such, the compensated thickness measurement for test object 500, $L_{Comp}$, can be determined by substituting Equation 12 into Equation 9, yielding Equation 13:

$$L_{Comp} = L_u \frac{(1 + \eta T)}{(1 + \eta T_{Comp})} \quad (13)$$

Equation 13, therefore, can be used to adjust the uncompensated thickness value measured by the ultrasonic testing system 100, $L_u$ for changes that occur to the thickness of test object 500 as a result of thermal expansion and temperature dependent ultrasonic velocity. Accordingly, the compensated thickness measurements can be used to directly compare different thickness measurements taken at different points in time regardless of the operating temperature of the test object 500, which generally varies over time. This allows normalized comparisons of thickness measurements to identify changes in thickness that might occur over time, such as those that would result from corrosion in a pipe.

In other embodiments, different regression analysis techniques can be used to apply a non-linear or some other mathematical fit to the experimental data. For example, a second order polynomial fit as shown in Equation 14 below could be used:

$$y = nx^2 + mx + b \tag{14}$$

For this case, the compensation equation would now be of the form of Equation 15, with a higher order compensation coefficient, $\kappa$.

$$h(T) = 1 + \eta T + \kappa T^2 \tag{15}$$

The regression values can then be related to the compensation coefficients as in Equations 16 and 17.

$$\eta = \frac{m}{b} \tag{16}$$

$$\kappa = \frac{n}{b} \tag{17}$$

Because of the strong thermocoupling between the delay line 120 and the test object 500, the temperature of the delay line 120 closely approximates that of the test object 500. Therefore, by calculating the temperature of the delay line 120, the operating temperature of the test object 500 can be determined. The same relationships between time of flight and temperature disclosed in Equations 1 through 17 that allow ultrasonic thickness measurements to be compensated for changes in temperature can also be used to determine the temperature of the delay line based on the measured time of flight. In particular, by combining Equations 6 and 12, a relationship between an ultrasonic time of flight in the delay line 120 at a calibration temperature, $T_{Cal}$, and the time of flight at another measurement temperature, T, can be determined, as shown in Equation 18:

$$\frac{t_{Cal}}{t} = \frac{(1 + \eta_{DL} T)}{(1 + \eta_{DL} T_{Cal})} \tag{18}$$

wherein,
$T_{Cal}$=the measured delay line 120 calibration temperature,
T=the delay line 120 measurement temperature,
$t_{Cal}$=the measured delay line 120 time of flight at the calibration temperature,
t=the delay line 120 time of flight at temperature T, and
$\eta_{DL}$=the delay line 120 compensation coefficient (an empirically determined constant).

Solving Equation 18 for T shows that the delay line 120 measurement temperature can be determined based on the delay line 120 time of flight at the measurement temperature, the delay line 120 time of flight at the calibration temperature, the delay line 120 calibration temperature, and the delay line 120 compensation coefficient, as shown in Equation 19:

$$T = \frac{1}{\eta_{DL}} \left[ \frac{t_{Cal}}{t} (1 + \eta_{DL} T_{Cal}) - 1 \right] \tag{19}$$

In order to determine T numerically, however, an initial set of data points is needed containing the measured delay line 120 calibration temperature, $T_{Cal}$, and the measured delay line 120 time of flight at the calibration temperature, $t_{Cal}$. To obtain this data, upon installation or at some other time, the delay line 120 of ultrasonic testing system 100 can be calibrated by independently measuring and storing the temperature of the delay line 120 using a thermocouple, pyrometer, or some other means. In addition, the delay line 120 time of flight at that calibration temperature is measured and stored in the ultrasonic testing system 100. The calibration measurements can be made either while the delay line 120 is attached or detached from the test object 500. With these data points, Equation 19 can be numerically solved using the measured delay line 120 time of flight at temperature T in order to determine the delay line 120 measurement temperature.

Accordingly, all temperature measurements of the delay line 120 following the initial delay line 120 calibration measurements can be performed automatically by the ultrasonic testing system 100 without the use of a thermocouple, pyrometer or other independent or integrated temperature measuring device. This eliminates the cost and complexity of having to install and maintain a hardware and software network solely to determine temperature. Knowing the temperature of the delay 120, the temperature of the test object 500 is also known, without the need for a separate temperature measuring device.

Furthermore, knowing the temperature of the test object 500 allows the ultrasonic testing system, using Equations 8 and 13, to determine a compensated thickness of the test object 500, thereby automatically adjusting the measured thickness measurement in response to the effects of thermal expansion and temperature dependent ultrasonic velocity. In turn, this improves the usability and accuracy of the measurements made by the ultrasonic testing system 100.

Although the embodiments of the invention shown and discussed herein for the most part perform the required calculations as a linear series of steps, it is clear that other embodiments can perform these steps either in different sequences or simultaneously to arrive at the same result.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for performing, ultrasonic testing using an ultrasonic testing system, the method comprising the steps of:
    positioning an ultrasonic transducer and a delay line on an outer wall of a test object;
    firing said ultrasonic transducer to generate an ultrasonic pulse that passes through said delay line and through said test object, a portion of said ultrasonic pulse being reflected back from an interface between said delay line and said outer wall of said test object;
    measuring a delay echo time of flight, wherein said delay echo time of flight is the time it takes for said ultrasonic pulse to travel from said ultrasonic transducer to said interface between said delay line and said outer wall of said test object and back as said reflected portion of said ultrasonic pulse;
    determining the temperature of said delay line based on only one time of flight measurement of said ultrasonic pulse that passes through said delay line, said only one time of flight measurement consisting of said delay echo time of flight; and determining the temperature of said test object based on the temperature of said delay line.

2. The method of claim 1, wherein the step of determining the temperature of said delay line using said delay echo time of flight comprises using said delay echo time of flight to find a corresponding temperature of said delay line in a stored table.

3. The method of claim 1, wherein the step of determining the temperature of said delay line using said delay echo time of flight comprises calculating the value of a transfer function using said delay echo time of flight.

4. The method of claim 3, wherein said transfer function is linear.

5. The method of claim 3, wherein said transfer function is non-linear.

6. The method of claim 1, wherein the temperature of said test object is the same as the temperature of said delay line.

7. The method of claim 1, further comprising the step of using said temperature of said test object to determine a thickness of said test object that is compensated for thermal expansion and temperature dependent ultrasonic velocity.

8. The method of claim 1, wherein said delay line is integral to said ultrasonic transducer.

9. The method of claim 1, wherein said delay line is separate from said ultrasonic transducer.

10. A method for performing ultrasonic testing using an ultrasonic testing system, the method comprising the steps of:
positioning an ultrasonic transducer and a delay line on an outer wall of a test object;
measuring a first temperature of said delay line;
firing said ultrasonic transducer to generate a first ultrasonic pulse that passes through said delay line and through said test object, a portion of said first ultrasonic pulse being reflected back from an interface between said delay line and said outer wall of said test object;
measuring a first delay echo time of flight, wherein said first delay echo time of flight is the time it takes for said first ultrasonic pulse to travel from said ultrasonic transducer to said interface between said delay line and said outer wall of said test object and back as said reflected portion of said first ultrasonic pulse;
firing said ultrasonic transducer to generate a second ultrasonic pulse that passes through said delay line and through said test object, a portion of said second ultrasonic pulse being reflected back from said interface between said delay line and said outer wall of said test object;
measuring a second delay echo time of flight, wherein said second delay echo time of flight is the time it takes for said second ultrasonic pulse to travel from said ultrasonic transducer to said interface between said delay line and said outer wall of said test object and back as said reflected portion of said second ultrasonic pulse;
determining a second temperature of said delay line based on only one time of flight measurement of said first ultrasonic pulse that passes through said delay line and only one time of flight measurement of said second ultrasonic pulse that passes through said delay line, said only one time of flight measurement of said first and second ultrasonic pulses consisting of said first and second delay echo times of flight, respectively, and based on said first temperature of said delay line; and
determining the temperature of said test object based on the second temperature of said delay line.

11. The method of claim 10, wherein the step of determining the second temperature of said delay line using said second delay echo time of flight comprises calculating the value of a transfer function using said second delay echo time of flight.

12. The method of claim 11, wherein said transfer function is linear.

13. The method of claim 11, wherein said transfer function is non-linear.

14. The method of claim 10, wherein the temperature of said test object is the same as the temperature of said delay line.

15. The method of claim 10, further comprising the step of using said temperature of said test object to determine a thickness of said test object that is compensated for thermal expansion and temperature dependent ultrasonic velocity.

16. The method of claim 10, wherein said delay line is integral to said ultrasonic transducer.

* * * * *

UNITED STATES PATENT AND TRADEMARK OFFICE
CERTIFICATE OF CORRECTION

PATENT NO. : 8,434,936 B2  Page 1 of 1
APPLICATION NO. : 12/580345
DATED : May 7, 2013
INVENTOR(S) : Cuffe et al.

It is certified that error appears in the above-identified patent and that said Letters Patent is hereby corrected as shown below:

In the Specifications:

In Column 6, Line 61, delete "$L_u$" and insert -- $L_u$, --, therefor.

In the Claims:

In Column 8, Line 51, in Claim 1, delete "performing," and insert -- performing --, therefor.

Signed and Sealed this
Twenty-fifth Day of June, 2013

Teresa Stanek Rea
*Acting Director of the United States Patent and Trademark Office*